United States Patent [19]

Morris et al.

[11] Patent Number: 4,946,860

[45] Date of Patent: Aug. 7, 1990

[54] BENZOTHIOPYRANYL DERIVATIVES AS HMG-COA REDUCTASE INHIBITORS

[75] Inventors: Robert L. Morris, Wayne; Jeffrey N. Barton, Philadelphia, both of Pa.

[73] Assignee: Rorer Pharmaceutical Corporation, Fort Washington, Pa.

[21] Appl. No.: 431,417

[22] Filed: Nov. 3, 1989

[51] Int. Cl.$^5$ .................. A61K 31/38; C07D 335/06
[52] U.S. Cl. .................. 514/432; 549/23
[58] Field of Search .................. 549/23; 514/432

[56] References Cited

U.S. PATENT DOCUMENTS

| | | | |
|---|---|---|---|
| 4,282,155 | 8/1981 | Smith et al. | 549/292 |
| 4,611,067 | 9/1986 | Volante et al. | 549/292 |
| 4,668,699 | 5/1987 | Hoffman et al. | 560/119 |
| 4,897,402 | 1/1990 | Duggan et al. | 549/23 |

FOREIGN PATENT DOCUMENTS 0290130  11/1988  European Pat. Off. .............. 549/23

Primary Examiner—Mary C. Lee
Assistant Examiner—M. S. Howard

Attorney, Agent, or Firm—Imre (Jim) Balogh; James A. Nicholson; Martin F. Savitzky

[57] ABSTRACT

Disclosed are novel benzothiopyranyl derivatives as 3-hydroxy-3-methylglutaryl-coenzyme A reductase inhibitors useful as antihypercholesterolemic agents represented by the formula:

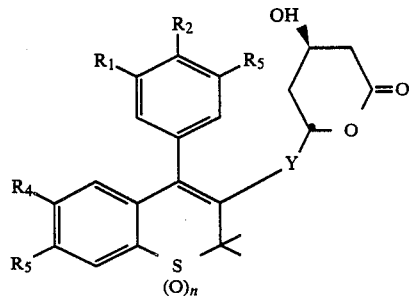

their corresponding dihydroxy acids, and pharmaceutically acceptable salts thereof.

5 Claims, No Drawings

BENZOTHIOPYRANYL DERIVATIVES AS HMG-COA REDUCTASE INHIBITORS

BACKGROUND OF THE INVENTION

1. Field of the Invention

The present invention relates to compounds, pharmaceutical compositions and a method useful for reducing serum cholesterol in humans. More particularly, the invention relates to benzothiopyranyl derivatives and pharmaceutically acceptable salts thereof which are potent inhibitors of the enzyme 3-hydroxy-3-methylglutaryl-coenzyme A reductase (hereinafter HMG-CoA reductase), pharmaceutical compositions thereof, and a method of inhibiting biosynthesis of cholesterol for the treatment of atherosclerosis, hyperlipidemia and hypercholesterolemia.

2. Reported Developments

Inhibitors of HMG-CoA reductase are effective in lowering blood plasma cholesterol level as well as inhibiting the biosynthesis of cholesterol in humans. As such, inhibitors of HMG-CoA reductase are useful in the prevention and treatment of coronary heart diseases. The prior art recognizes the importance of such compounds, e.g., Bethridge et al., Brit. Med. J., 4,500 (1975) and Brown et al., Scientific American, 58 Nov. (1984). Illustrative references directed to such compounds follow.

U.S. Pat. No. 4,681,893 to B. D. Roth pertains to trans-6-[2-(3-or 4-carboxamido-substituted pyrrol-1-yl)alkyl]-4-hydroxy-pyran-2-ones useful as hypocholesterolemic agents.

U.S. Pat. No. 4,668,699 to Hoffman et al. discloses semi-synthetic analogs of compactin and mevinolin and the dihydro and tetrahydro analogs thereof for antihypercholesterolemic application.

U.S. Pat. No. 4,282,155 to Smith et al. is directed to 6(R)-[2-(8'-etherified-hydroxy-2',6'-dimethylpolyhydro-1'-naphthyl)ethyl]-4(R)-hydroxy-3,4,5,6-tetrahydro-2H-pyran-2-ones for inhibition of biosynthesis of cholesterol.

U.S. Pat. No. 4,567,289 relates to methyl, ethyl, n-propyl, 2-(acetylamino)ethyl, or 1-(2,3-dihydroxy)propyl ester of E-(3R,5S)-7-(4'-fluoro-3,3',5-trimethyl[1,1'-biphenyl]-2-yl)-3,5-dihydroxy-6-heptenoic acid that are HMG-CoA reductase inhibitors.

U.S. Pat. No. 4,611,067 discloses a process for the preparation of HMG-CoA reductase inhibitors which contain a 4-hydroxy-3,4,5,6-tetrahydro-2H-pyran-2-one moiety.

SUMMARY OF THE INVENTION

The present invention comprises benzothiopyranyl derivatives of the formula:

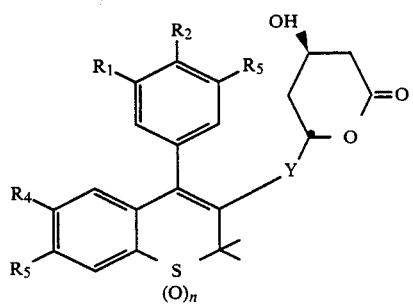

wherein:
$R_1$ is H,
  alkyl,
  hydroxyalkyl,
  alkoxy or
  $CF_3$;
$R_2$ is H,
  Cl,
  F,
  Br,
  I,
  alkoxy or
  $CF_3$;
$R_3$ is H,
  alkyl,
  Cl,
  F,
  Br,
  I,
  alkoxy or
  $CF_3$;
$R_4$ and $R_5$ are independently
  H,
  alkyl or
  alkoxy;
Y is CH=CH or
  $CH_2$—$CH_2$;
n is 0, 1 or 2;
their corresponding dihydroxy acids; and
pharmaceutically acceptable salts thereof.

The invention also comprises pharmaceutical compositions comprising the aforesaid compounds useful for reducing serum cholesterol in humans.

Another aspect of this invention comprises a method for inhibiting cholesterol biosynthesis in humans by administering an aforesaid compound or composition.

DETAILED DESCRIPTION OF THE INVENTION

As employed above and throughout the specification, the following terms, unless otherwise indicated, shall be understood to have the following meaning:

"Alkyl" means a saturated or unsaturated aliphatic hydrocarbon which may be either straight- or branched-chained containing from about one to about ten, and preferably one to six carbon atoms.

"Hydroxyalkyl" means an alkyl group substituted by a hydroxy group. Hydroxy lower alkyl groups are preferred. Exemplary preferred groups include hydroxymethyl, 2-hydroxyethyl, 2-hydroxypropyl and 3-hydroxypropyl.

"Alkoxy" means an alkyl-oxy group in which alkyl is as previously described. Lower alkoxy groups are preferred. Exemplary groups include methoxy, ethoxy, n-propoxy, i-propoxy and n-butoxy.

The compounds of this invention may be useful in the form of the free acid, in the form of salts and as a hydrate. All forms are within the scope of the invention.

The pharmaceutically acceptable salts of the present invention include those formed from sodium, potassium, calcium, aluminum, lithium, magnesium, zinc, lysine, arginine, procaine, ethylenediamine and piperazine.

The invention encompasses optical and stereoisomers of the compounds and mixtures thereof defined by the structural formula.

A reaction scheme procedure for preparing the compounds of the present invention is as shown:

REACTION SCHEME

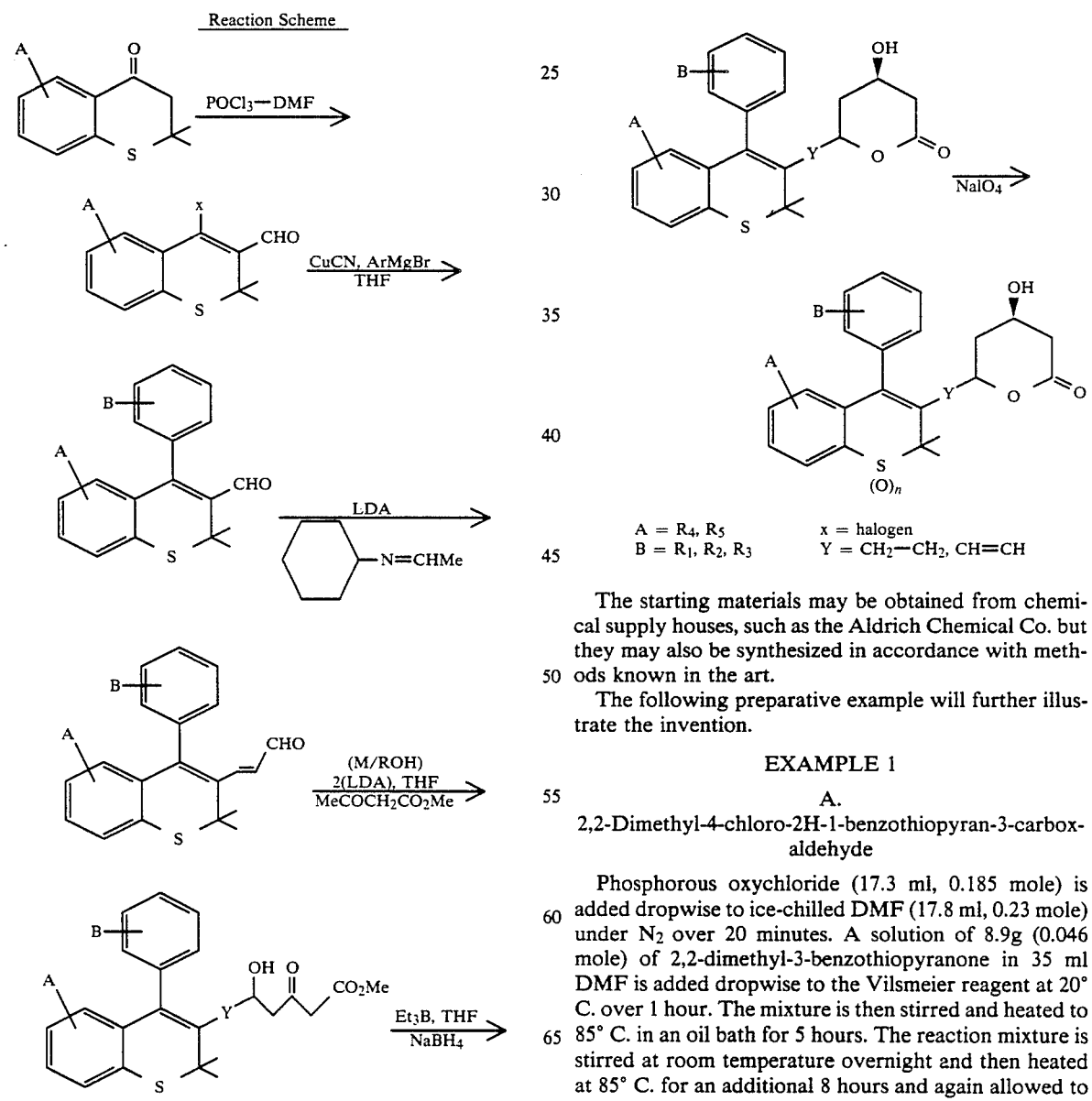

A = $R_4$, $R_5$
B = $R_1$, $R_2$, $R_3$
x = halogen
Y = $CH_2$—$CH_2$, $CH$=$CH$ The starting materials may be obtained from chemical supply houses, such as the Aldrich Chemical Co. but they may also be synthesized in accordance with methods known in the art.

The following preparative example will further illustrate the invention.

EXAMPLE 1

A.
2,2-Dimethyl-4-chloro-2H-1-benzothiopyran-3-carboxaldehyde

Phosphorous oxychloride (17.3 ml, 0.185 mole) is added dropwise to ice-chilled DMF (17.8 ml, 0.23 mole) under $N_2$ over 20 minutes. A solution of 8.9g (0.046 mole) of 2,2-dimethyl-3-benzothiopyranone in 35 ml DMF is added dropwise to the Vilsmeier reagent at 20° C. over 1 hour. The mixture is then stirred and heated to 85° C. in an oil bath for 5 hours. The reaction mixture is stirred at room temperature overnight and then heated at 85° C. for an additional 8 hours and again allowed to stir at room temperature overnight.

The reaction mixture is poured into a 40% sodium acetate solution and stirred 1 hour. This mixture is extracted with hexane, and the organic layer is washed with water, dried over MgSO$_4$ and concentrated to give 6.7g residue. Purification is accomplished via HPLC (100:1, hexane:EtOAc), giving 3.43g (31%) of the desired product which solidified upon standing to form a yellow crystalline solid; m.p. 49°–52° C.

B. 2,2-Dimethyl-4-(4-fluorophenyl)-2H-1-benzothiopyran-3-carboxaldehyde

Cuprous cyanide (3.4g, 0.038 mole) is added to 120 ml anhydrous THF, under N$_2$, and cooled to −10° C. Then 4-fluorophenyl magnesium bromide (1M, 36 ml) is added dropwise over 25 minutes at −10° C. This mixture is stirred for 10 minutes and 4.3g of the compound obtained in Example 1A (0.018 mole) dissolved in 40 ml THF, is added dropwise over 1.25 hours keeping the reaction temperature between −5° and −10° C. The reaction mixture is stirred for 0.5 hours following the addition.

The reaction mixture is slowly poured into cold saturated NH$_4$Cl solution and the organic layer washed with NH$_4$Cl solution, then dried over MgSO4 and concentrated, giving 6.25g crude residue. Isolation is accomplished on HPLC (100:1, hexane:EtOAc). 2.19g of pure material is obtained (41% yield).

C. (E)-3-[2,2-Dimethyl-4-(4-fluorophenyl)-2H-1-benzothiopyran-3-yl]-2-propenaldehyde To a solution of diisopropylamine (1.46 ml, 0.01 mole) in 15 ml anhydrous THF, under N$_2$ and cooled to −70° C., is added dropwise n-BuLi (2.5M, 3.8 ml) over 10 minutes. This mixture is stirred for 5 minutes and then ethylidene cyclohexylamine (1.2g, 0.0095 mole) in 15 ml THF is added dropwise over 20 minutes at −50° C. The reaction mixture is then stirred at −20° C. for 40 minutes.

The reaction mixture is cooled to −70° C. again and 1.78g of the compound obtained in Example 1B (0.006 mole), in 20 ml THF, is added thereto dropwise over 1 hour. The reaction mixture is then stirred for 1 hour at 0° C. The reaction mixture is then added to 100 ml water and extracted twice with ether. The organic layer is dried over MgSO$_4$ and concentrated to give 2.71g crude residue. This is chromatographed on silica gel (20:1, hexane:EtOAc) and 0.88g of pure product is obtained (45% yield).

D. Methyl (E)-7-[2,2-dimethyl-4-(4-fluorophenyl)-2H-1-benzothiopyran-3-yl]-5-hydroxy-3-oxo-6-heotenoate To a solution of diisopropylamine (1.63 ml, 0.012 mole) dissolved in 15 ml anhydrous THF, cooled to −78° C. and under N$_2$, is added n-BuLi (2.5M, 4.25 ml) dropwise over 10 minutes. This mixture is stirred for 5 minutes then methyl acetoacetate (0.51 ml, 0.0047 mole) in 10 ml THF is added dropwise over 20 minutes. When the addition is completed, the cooling bath is removed, the reaction temperature is allowed to reach −10° C. and then an ice bath is used to maintain 0° C. for 1.5 hours.

At this point 1.2g (0.0037 mole) of the compound obtained in Example 1C in 15 ml anhydrous THF is added to the reaction mixture over 30 minutes. The reaction mixture is stirred for 1 hour following the completion of the addition. Glacial acetic acid (1.3 ml) in 10 ml THF is added dropwise over 10 minutes, then the reaction mixture is poured into EtOAc, washed with water, NaHCO$_3$ solution and finally brine, then dried over MgSO$_4$ and concentrated to give 1.48g residue. This is chromatographed on silica gel with EtOAc:hexane (15:85 to 50:50) and the desired product is obtained in 30% yield (0.5g).

E. Methyl (3R*, 5S*)-(E)-7-[2,2-dimethyl-4-(4-fluorophenyl)-2H-1-benzothiopyran-3-yl]-3,5-dihydroxy-6-heotenoate To a solution of the compound obtained in Example 1D (0.44g, 0.001 mole) in 10 ml anhydrous THF is added a 1M solution of triethylborane (1.5 ml, 0.0015 mole) over 5 minutes and then stirred for an additional 5 minutes. The reaction mixture is then cooled to −78° C. and sodium borohydride (0.05g, 0.0013 mole) added all at once, followed by the dropwise addition of MeOH (0.44 ml) in 5 ml THF over 30 minutes and at −78° C. The reaction mixture is then stirred at this temperature for 0.5 hours, then stirred at −55° C. for an additional 0.5 hours. The cooling bath is removed and when the reaction temperature reaches −10° C., a solution of 30% H$_2$O$_2$ (2.13 ml) in 1 ml of water is added over 5 minutes. This mixture is stirred at room temperature for 0.5 hours and poured into 50 ml EtOAc. The organic layer is then successively washed with 1N HCl, NaHCO$_3$ solution and brine, then dried over MgSO$_4$ and concentrated to give 0.41g residue (90%). This material is used in the following step without further purification.

F. (3R*,5S*)-(E)-7-[2,2-Dimethyl-4-(4-fluorophenyl)-2H-1-benzothiopyran-3-yl-3,5-dihydroxy-6-heptenoic acid 0.4g (0.0009 mole) of the compound obtained in Example 1E is dissolved in 10 ml EtOH and to this is added 1.08 ml of 1M NaOH dropwise over 15 minutes. This mixture is stirred for 0.5 hours and the reaction mixture is then concentrated to dryness and the residue dissolved in water. Acidification to pH 1 with concentrated HCl is followed by extraction with chloroform. This extract is washed with brine, dried over MgSO$_4$ and concentrated to give 0.28g residue (73% yield). This material is used directly in the next step without further purification.

G. Trans-(E)-6-[2-[2,2-dimethyl-4-(4-fluorophenyl)-2H-1-benzothiopyran-3-yl]ethenyl-3,4,5,6-tetrahydro-4-hydroxy-2H-pyran-2-one 0.28g (0.00065 mole) of the compound obtained in Example 1F is dissolved in 15 ml chloroform and to this is added triethylamine (0.11 ml, 0.00078 mole). This solution is cooled in ice to 3° C. and ethyl chloroformate (0.065 ml, 0.00065 mole) in 5 ml CHCl$_3$ is added dropwise over 5 minutes maintaining a reaction temperature of 2°–3° C. This is stirred for 15 minutes and then the reaction mixture is poured into 50 ml water and the organic layer washed with NaHCO$_3$ solution and brine, then dried over MgSO$_4$ and concentrated to give 0.2g residual solid. Purification is accomplished via flash chromatography (40% EtOAc/hexane) followed by recrystallization from EtOAc to give a white solid; m.p. 192°–193.5° C. (0.04g, 15% yield).

Elemental Analysis: Calculated for C$_{24}$H$_{23}$FO$_3$S: C, 70.22; H, 5.65%; Found: C, 70.01; H, 5.52%.

Employing the Reaction Scheme and using analogous procedures to that used in Example 1, the following compounds are prepared:

Trans-(E)-6-[2-[2,2-dimethyl-4-(4-fluorophenyl)-2H-1-benzothiopyran-3-yl]ethenyl]-3,4,5,6-tetrahydro-4-hydroxy-2H-pyran-2-one-1,1-dioxide;

Trans-(E)-6-[2-[2,2-dimethyl-4-(4-fluoro-3-methylphenyl)-2H-1-benzothiopyran-3-yl]ethenyl]-3,4,5,6-tetrahydro-4-hydroxy-2H-pyran-2-one;

Trans-(E)-6-[2-[6,7-dimethoxy-2,2-dimethyl-4-(4-fluorophenyl)-2H-1-benzothiopyran-3-yl]ethenyl]-3,4,5,6-tetrahydro-4-hydroxy-2H-pyran-2-one;

Trans-(E)-6-[2-[2,2-dimethyl-4-(3,5-dimethylphenyl)-2H-1-benzothiopyran-3-yl]ethenyl]-3,4,5,6-tetrahydro-4-hydroxy-2H-pyran-2-one;

Trans-(E)-6-[2-[2,2-dimethyl-4-[4-fluoro-3-(hydroxymethyl)-phenyl]-2H-1-benzothiopyran-3-yl]ethenyl]-3,4,5,6-tetrahydro-4-hydroxy-2H-pyran-2-one;

Trans-6-[2-[2,2-dimethyl-4-(4-fluoro-3-methylphenyl)-2H-1-benzothiopyran-3-yl]ethyl]-3,4,5,6-tetrahydro-4-hydroxy-2H-pyran-2-one;

Trans-(E)-6-[2-[2,2-dimethyl-4-(4-fluorophenyl)-2H-1-benzothiopyran-3-yl]ethenyl]-3,4,5,6-tetrahydro-4-hydroxy-2H-pyran-2-one-1-oxide;

Trans-(E)-6-[2-[2,2-dimethyl-4-(4-fluoro-3-methylphenyl)-2H-1-benzothiopyran-3-yl]ethenyl]-3,4,5,6-tetrahydro-4-hydroxy-2H-pyran-2-one-1,1-dioxide;

Trans-(E)-6-[2-[2,2-dimethyl-4-(4-fluoro-3-methylphenyl)-2H-1-benzothiopyran-3-yl]ethenyl]-3,4,5,6-tetrahydro-4-hydroxy-2H-pyran-2-one-1-oxide;

Trans-(E)-6-[2-[6,7-dimethoxy-2,2-dimethyl-4-(4-fluorophenyl)-2H-1-benzothiopyran-3-yl]ethenyl]-3,4,5,6-tetrahydro-4-hydroxy-2H-pyran-2-one-1,1-dioxide;

Trans-6-[2-[2,2-dimethyl-4-(4-fluoro-3-methylphenyl)-2H-1-benzothiopyran-3-yl]ethyl]-3,4,5,6-tetrahydro-4-hydroxy-2H-pyran-2-one-1,1-dioxide; and Trans-(E)-6-[2-[2,2-dimethyl-4-(3,5-dimethylphenyl)-2H-1-benzothiopyran-3-yl]ethenyl]-3,4,5,6-tetrahydro-4-hydroxy-2H-pyran-2-one-1-oxide.

The compounds of the present invention are useful as hypocholesterolemic or hypolipidemic agents by virtue of their ability to inhibit the biosynthesis of cholesterol through inhibition of the enzyme HMG-CoA reductase. Having such ability, the compounds are incorporated into pharmaceutically acceptable carriers and administered to a patient in need of such cholesterol biosynthesis inhibition orally or parenterally. Such pharmaceutical formulations are to contain at least one compound according to the invention.

Suitable carriers include diluents or fillers, sterile aqueous media and various non-toxic organic solvents. The compositions may be formulated in the form of tablets, capsules, lozenges, trochees, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers.

Where aqueous suspensions for oral use are formulated, the carrier can be emulsifying or suspending agents. Diluents such as ethanol, propylene glycol, and glycerin and their combinations can be employed as well as other materials.

For parenteral administration, solutions or suspensions of these compounds in aqueous alcoholic media or in sesame or peanut oil or aqueous solutions of the soluble pharmaceutically acceptable salves can be employed.

The dosage regimen in carrying out the methods of this invention is that which insures maximum therapeutic response until improvement is obtained and thereafter the minimum effective level which gives relief. Doses may vary, depending on the age, severity, body weight and other conditions of the patients but are ordinarily in the area of 5 mg/kg to 500 mg/kg of body weight in oral administration; such may, of course, be given in two to four divided doses. With other forms of administration equivalent or adjusted doses will be administered depending on the route of administration.

The utility of the claimed compounds is measured by the test methods described hereunder. The methods are based on the articles: "Purification of 3-Hydroxy-3-Methylglutaryl-Coenzyme A Reductase From Rat Liver" by Kleinsek et al., Proc. Natl. Acad. Sci. USA, Vol. 74, pp. 1431-1435, April 1977 Biochemistry; "Mevinolin: A Highly Potent Competitive Inhibitor of Hydroxy Methyl Glutaryl-Coenzyme A Reductase and a Cholesterol-Lowering Agent" by Alberts et al., Proc. Natl. Acad. Sci. USA, Vol. 77, pp. 3951-3961, July 1980, Biochemistry; "Effects of ML-236B on Cholesterol Metabolism in Mice and Rats: Lack of Hypocholesterolemic Activity in Normal Animals" by Endo et al., Biochemica et Biophysica Acta, 575 (1979) 266-276; and "Evidence of Regulation of 3-Hydroxy-3-Methylglutaryl Coenzyme A Reductase Activity and Cholesterol Synthesis in Nonhepatic Tissues of Rat" by Balasubramaniam et al., Proc. Natl. Acad. Sci. USA, Vol. 73, No. 8, pp. 2564-2568, Aug. 1976, Biochemistry.

The first method used (designated HMGR Screen) was as follows: Male rats were acclimated to an alternate 12 hour light-dark cycle for a period of 2-3 weeks. The animals, weighing 180-230g, were fed ad libitum a rat chow containing 2% cholestyramine for 5 days prior to sacrifice at the mid-dark period. Liver microsomes were prepared and HMGR enzyme was solubilized from the microsomes by freeze-thaw manipulation in high ionic strength buffer. The enzyme preparation was stored at $-80°$ C. in 300 $\mu l$ portion samples. Prior to use, the enzyme was activated at 37° C. for 30 minutes in a reaction mixture. The reaction mixture was contained in a volume of 240 $\mu l$ 1:0.14M potassium phosphate buffer (pH 7.0); 0.18M KCl; 3.5 mM EDTA; 10 mM dithiothreitol; 0.1 mg/ml BSA; 30,000 cpm of [$^{14}$C] HMG-CoA; 20 $\mu$M HMG-CoA; and 200 $\mu$g of solubilized enzyme with and without inhibitors (in 10 $\mu l$ DMSO). After 5 minutes incubation at 37° C. the reaction was initiated with 0.2 mM NADPH. The final assay volume was 300 μl. After 10 minutes the reaction mixture was terminated with 100 μl of 1N HCl. After an additional incubation for 15 minutes at 37° C. to allow for complete lactonization of the product, the mixture was diluted with 3 ml GDW. The diluted mixture was then poured over a 0.7×1.4 cm column containing 100-200 mesh Bio-Rex ion-exchange resin (chloride form of Bio-Rad) which was equilibrated with distilled water. With this resin the unreacted [$^{14}$C] HMG-CoA was adsorbed and the product [$^{14}$C] lactone was eluted (80% recovery) directly into scintillation vials. After the addition of 10 ml of Aquasol, radioactivities of the samples were measured in a scintillation counter. The compound of Example 1G showed an IC$_{50}$ value of 9.8 nM per liter.

The second method used (designated Ex-Vivo Non-Fasted and Ex-Vivo Fasted) used was as follows: Rats of 170-210g were maintained on a low cholesterol diet for one week prior to use. Drugs were given orally in 0.5% methocel to both fed and fasted (fasted for 16 hours) rats. After one hour (fasted rats) and two hours (fed rats) the rats were decapitated and their livers removed and transferred to chilled oxygenated Kreb's-Ringer-bicarbonate buffer (pH 7.4). The livers were then chopped into 0.5 mm slices using a McIlwain tissue chopper, and were suspended in the same buffer. Aliquots of the suspension containing 100 mg tissue were pipetted to culture tubes which contained [$^{14}$C] sodium acetate (2 μCi, 1 mM). The tubes were gassed with 95% O$_2$/5%CO$_2$, capped and incubated at 37° C. in a shaking water bath at 150 oscillation/minute for two hours. The final assay volume was 1.0 ml. After incubation the reaction was stopped by the addition of 1.0 ml of 15% KOH in ethanol, and the internal standard $^3$H-cholesterol was added. The tubes were recapped and the samples were saponified at 75° C. for two hours with periodic mixing. Subsequently an aliquot was removed for protein analysis using Bio-Rad's standard kit, and the remainder of the saponified samples was extracted with 10 ml of petroleum ether for 30 minutes. The lower aqueous phase was frozen in a dry ice/alcohol mixture and the ether layer was poured into labelled tubes. The ether was then evaporated to dryness and the cholesterol was separated by thin layer chromatography on plastic silica gel plates. After visualization with iodine the cholesterol spots were cut and counted with liquid scintillation fluid. The compound of Example 1G inhibited 43% of cholesterol synthesis in the non-fasted rats.

What is claimed is:

1. A compound of the formula

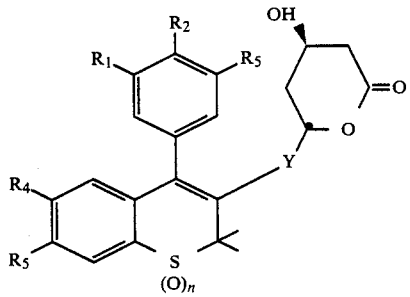

wherein:
R$_1$ is H,
alkyl,
hydroxyalkyl,
alkoxy or
CF$_3$;
R$_2$ is H,
Cl,
F,
Br,
I,
alkoxy or
CF$_3$;
R$_3$ is H,
alkyl,
Cl,
F,
Br,
I,
alkoxy or
CF$_3$;
R$_4$ and R$_5$ are independently
H,
alkyl or
alkoxy;
Y is CH=CH or CH$_2$—CH$_2$;
n is 0, 1 or 2;
or a corresponding dihydroxy acid; or a pharmaceutically acceptable salt thereof.

2. A pharmaceutical composition comprising a therapeutically effective amount of a compound of claim 1, and a pharmaceutically acceptable carrier.

3. The pharmaceutical composition of claim 2 wherein said compound is selected from the group consisting of:
Trans-(E)-6-[2-[2,2-dimethyl-4-(4-fluorophenyl)-2H-1-benzothiopyran-3-yl]ethenyl]-3,4,5,6-tetrahydro-4-hydroxy-2H-pyran-2-one;
Trans-(E)-6-[2-[2,2-dimethyl-4-(4-fluorophenyl)-2H-1-benzothiopyran-3-yl]ethenyl]-3,4,5,6-tetrahydro-4-hydroxy-2H-pyran-2-one-1,1-dioxide;
Trans-(E)-6-[2-[2,2-dimethyl-4-(4-fluoro-3-methylphenyl)-2H-1-benzothiopyran-3-yl]ethenyl]-3,4,5,6-tetrahydro-4-hydroxy-2H-pyran-2-one;
Trans-(E)-6-[2-[6,7-dimethoxy-2,2-dimethyl-4-(4-fluorophenyl)-2H-1-benzothiopyran-3-yl]ethenyl]-3,4,5,6-tetrahydro-4-hydroxy-2H-pyran-2-one; and
Trans-(E)-6-[2-[2,2-dimethyl-4-(3,5-dimethylphenyl)-2H-1-benzothiopyran-3-yl]ethenyl]-3,4,5,6-tetrahydro-4-hydroxy-2H-pyran-2-one.

4. The pharmaceutical composition of claim 2 wherein said compound is selected from the group consisting of:
Trans-(E)-6-[2-[2,2-dimethyl-4-[4-fluoro-3-(hydroxymethyl)-phenyl]-2H-1-benzothiopyran-3-yl]ethenyl]-3,4,5,6-tetrahydro-4-hydroxy-2H-pyran-2-one;
Trans-6-[2-[2,2-dimethyl-4-(4-fluoro-3-methylphenyl)-2H-1-benzothiopyran-3-yl]ethyl]-3,4,5,6-tetrahydro-4-hydroxy-2H-pyran-2-one;
Trans-(E)-6-[2-[2,2-dimethyl-4-(4-fluorophenyl)-2H-1-benzothiopyran-3-yl]ethenyl]-3,4,5,6-tetrahydro-4-hydroxy-2H-pyran-2-one-1-oxide;
Trans-(E)-6-[2-[2,2-dimethyl-4-(4-fluoro-3-methylphenyl)-2H-1-benzothiopyran-3-yl]ethenyl]-3,4,5,6-tetrahydro-4-hydroxy-2H-pyran-2-one-1,1-dioxide;
Trans-(E)-6-[2-[2,2-dimethyl-4-(4-fluoro-3-methylphenyl)-2H-1-benzothiopyran-3-yl]ethenyl]-3,4,5,6-tetrahydro-4-hydroxy-2H-pyran-2-one-1-oxide;

Trans-(E)-6-[2-[6,7-dimethoxy-2,2-dimethyl-4-(4-fluorophenyl)-2H-1-benzothiopyran-3-yl]ethenyl]-3,4,5,6-tetrahydro-4-hydroxy-2H-pyran-2-one-1,1-dioxide;

Trans-6-[2-[2,2-dimethyl-4-(4-fluoro-3-methylphenyl)-2H-1-benzothiopyran-3-yl]ethyl]-3,4,5,6-tetrahydro-4-hydroxy-2H-pyran-2-one-1,1-dioxide; and Trans-(E)-6-[2-[2,2-dimethyl-4-(3,5-dimethylphenyl)-2H-1-benzothiopyran-3-yl]ethenyl]-3,4,5,6-tetrahydro-4-hydroxy-2H-pyran-2-one-1-oxide.

5. A method of inhibiting cholesterol biosynthesis in a patient in need of such treatment comprising administering a pharmaceutical composition defined in claim 2.

* * * * *